United States Patent
Chae et al.

(10) Patent No.: US 12,180,389 B2
(45) Date of Patent: Dec. 31, 2024

(54) TRICYCLODECANE DIMETHANOL COMPOSITION AND PREPARATION METHOD OF THE SAME

(71) Applicant: SK CHEMICALS CO., LTD., Gyeonggi-do (KR)

(72) Inventors: Hee Il Chae, Gyeonggi-do (KR); Ju-Sik Kang, Gyeonggi-do (KR); Jeong Ho Park, Gyeonggi-do (KR); Song Lee, Gyeonggi-do (KR); Yu Mi Chang, Gyeonggi-do (KR)

(73) Assignee: SK Chemicals Co., Ltd., Seongnam (KR)

(*) Notice: Subject to any disclaimer, the term of this patent is extended or adjusted under 35 U.S.C. 154(b) by 0 days.

(21) Appl. No.: 18/003,452

(22) PCT Filed: May 20, 2022

(86) PCT No.: PCT/KR2022/007239
§ 371 (c)(1),
(2) Date: Dec. 27, 2022

(87) PCT Pub. No.: WO2023/277347
PCT Pub. Date: Jan. 5, 2023

(65) Prior Publication Data
US 2023/0279243 A1 Sep. 7, 2023

(30) Foreign Application Priority Data
Jun. 29, 2021 (KR) .................. 10-2021-0084939

(51) Int. Cl.
*C07C 29/141* (2006.01)
*C07C 29/04* (2006.01)
*C07C 31/27* (2006.01)
*C07C 35/37* (2006.01)
*C07C 45/50* (2006.01)
*C09D 7/20* (2018.01)

(52) U.S. Cl.
CPC .............. *C09D 7/20* (2018.01); *C07C 29/04* (2013.01); *C07C 29/141* (2013.01); *C07C 31/278* (2013.01); *C07C 35/37* (2013.01); *C07C 45/50* (2013.01); *C07C 2603/68* (2017.05)

(58) Field of Classification Search
CPC ..... C07C 29/141; C07C 31/278; C07C 45/50; C07C 2603/68
See application file for complete search history.

(56) References Cited

U.S. PATENT DOCUMENTS

| | | | |
|---|---|---|---|
| 6,365,782 B1 * | 4/2002 | Nakamura | C07C 29/141 568/822 |
| 10,538,472 B1 | 1/2020 | Chou et al. | |
| 10,767,004 B1 | 9/2020 | Chiu et al. | |
| 2005/0107644 A1 | 5/2005 | Lappe et al. | |
| 2005/0272960 A1 | 12/2005 | Dukat et al. | |
| 2021/0253507 A1 | 8/2021 | Chae et al. | |

FOREIGN PATENT DOCUMENTS

| | | | | |
|---|---|---|---|---|
| EP | 3808728 A1 * | 4/2021 | | B01J 23/464 |
| KR | 10-2005-0044847 | 5/2005 | | |
| KR | 10-2006-0048238 | 5/2006 | | |
| KR | 10-1200288 | 11/2012 | | |
| KR | 10-2019-0142208 | 12/2019 | | |
| KR | 10-2020-0136484 | 12/2020 | | |
| WO | WO-2019240415 A1 * | 12/2019 | | B01J 23/464 |

OTHER PUBLICATIONS

Lange et al., "Three times faster to gel point," Adhesion Adhesives & Sealants, vol. 13, 2016, pp. 14-19.
International Search Report and Written Opinion for International (PCT) Patent Application No. PCT/KR2022/007239, dated Aug. 29, 2022, 7 pages.

* cited by examiner

*Primary Examiner* — Rosalynd A Keys
(74) *Attorney, Agent, or Firm* — Sheridan Ross P.C.

(57) ABSTRACT

Provided are a tricyclodecane dimethanol composition, in which a ratio of isomers is controlled, and a preparation method thereof.

7 Claims, No Drawings

TRICYCLODECANE DIMETHANOL COMPOSITION AND PREPARATION METHOD OF THE SAME

CROSS-REFERENCE TO RELATED APPLICATION

This application is a national stage application under 35 U.S.C. 371 and claims the benefit of PCT Application No. PCT/KR2022/007239 having an international filing date of 20 May 2022, which designated the United States, and which PCT application claimed the benefit of Korean Patent Application No. 10-2021-0084939, filed on Jun. 29, 2021, the contents of each of which are incorporated herein by reference in their entireties.

TECHNICAL FIELD

The present invention relates to a tricyclodecane dimethanol composition, in which a ratio of isomers is controlled, and a preparation method thereof.

BACKGROUND ART

Tricyclodecane dimethanol (3(4),8(9)-dihydroxymethyl-tricyclo[$5.2.1.0^{2,6}$]decane, TCDDM) is a material used as a monomer in the preparation of polymers such as polyester, polyacrylate, etc.

Tricyclodecane dimethanol may be prepared by performing hydroformylation of dicyclopentadiene (DCPD) to prepare tricyclodecane dialdehyde (TCDDA), followed by hydrogenation thereof, as disclosed in Korean Patent No. 10-1200288.

TCDDM prepared by such a method is a mixture of various structural isomers and stereoisomers, and a polyester resin prepared using the same is characterized in that its crystallization is difficult. Therefore, it is suitable for use as a coating agent for coating the inner surface of a can, etc.

When resins for coating the inner surface of a can have good solubility in organic solvents or water, it is preferable in that they may exhibit high processability. After a coating film is formed, it should not be hydrolyzed even under high temperature and high pressure conditions as in a sterilization process, and should maintain excellent physical properties. Accordingly, it is necessary to develop a TCDDM composition capable of producing a polyester resin suitable for coating the inner surface of a can.

PRIOR ART DOCUMENT

Patent Document 1: Korean Patent No. 10-1200288

DISCLOSURE

Technical Problem

There are provided a tricyclodecane dimethanol composition, in which a ratio of isomers is controlled, the tricyclodecane dimethanol composition capable of providing a polyester having excellent solubility in organic solvents and exhibiting excellent hot water resistance when forming a coating film, and a preparation method thereof.

Technical Solution

To achieve the above objects, there is provided a tricyclodecane dimethanol composition including A) octahydro-4,7-methano-1H-indene-$1_{eq}$,$6_{eq}$-dimethanol;

B) octahydro-4,7-methano-1H-indene-$3_{eq}$,$6_{eq}$-dimethanol;

C) octahydro-4,7-methano-1H-indene-$2_{eq}$,$6_{eq}$-dimethanol; and

D) octahydro-4,7-methano-1H-indene-$2_{ax}$,$6_{eq}$-dimethanol, wherein a weight ratio of (A+B+C)/D is 10 to 200.

There is also provided a method of preparing the tricyclodecane dimethanol composition, the method including the step of:

performing a hydrogenation reaction of tricyclodecane dialdehyde in the presence of a hydrogenation catalyst including a support and a catalyst metal supported on the support, wherein the support includes one or more elements selected from the group consisting of K, Na, Cr, Fe, Al, Mn, Ba, Si, Zn, Ca, and Bi, and the catalyst metal is one or more selected from the group consisting of Ru, Pd, Pt, Rh, Ni, Cu, and V.

Effect of the Invention

A tricyclodecane dimethanol composition of the present invention, in which a ratio of isomers is controlled, may be suitably used in preparing a polyester having excellent solubility in organic solvents and exhibiting excellent hot water resistance when forming a coating film. In addition, according to a method of preparing the tricyclodecane dimethanol composition of the present invention, it is possible to prepare the tricyclodecane dimethanol composition with high efficiency and yield.

BEST MODE FOR CARRYING OUT THE INVENTION

Hereinafter, the present invention will be described in detail.

Tricyclodecane Dimethanol Composition

A tricyclodecane dimethanol composition of the present invention includes four types of tricyclodecane dimethanol (TCDDM) isomers of A) octahydro-4,7-methano-1H-indene-$1_{eq}$,$6_{eq}$-dimethanol;

B) octahydro-4,7-methano-1H-indene-$3_{eq}$,$6_{eq}$-dimethanol;

C) octahydro-4,7-methano-1H-indene-$2_{eq}$,$6_{eq}$-dimethanol; and

D) octahydro-4,7-methano-1H-indene-$2_{ax}$,$6_{eq}$-dimethanol.

The 'eq' and 'ax' indicate the orientation of the dimethanol functional group, wherein 'eq' indicates the equatorial direction, and 'ax' indicates the axial direction.

Specifically, the component A is a compound represented by the following Formula 1-1, the component B is a compound represented by the following Formula 1-2, the component C is a compound represented by the following Formula 1-3, and the component D is a compound represented by the following Formula 1-4:

[Formula 1-1]

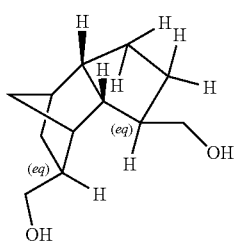

[Formula 1-2]

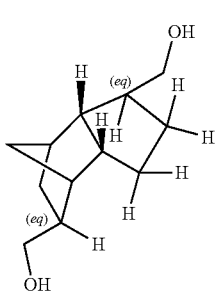

[Formula 1-3]

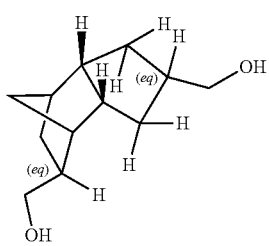

[Formula 1-4]

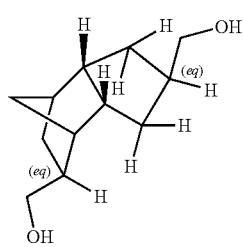

in Formulae 1-1 to 1-4, the 'eq' and 'ax' are marked to indicate the orientation of the dimethanol functional group.

Tricyclodecane dimethanol (TCDDM) may be prepared by reducing tricyclodecane dialdehyde (TCDDA), which may be prepared from a hydroformylation reaction of dicyclopentadiene (DCPD).

In such a preparation process, a number of TCDDA structural isomers and stereoisomers are produced due to the form (endo or exo) of DCPD, the position where the formyl group is bound to DCPD during hydroformylation, etc. Through this hydrogenation reaction of the TCDDA isomer mixture, a TCDDM composition is prepared, in which various structural isomers and stereoisomers are mixed.

The present inventors have studied a tricyclodecane dimethanol composition suitable for use as a monomer in the preparation of a polyester for coating, and as a result, they found that when the tricyclodecane dimethanol composition including the four types of isomers in a predetermined ratio is used in the preparation of a polyester, solubility of the polyester may be further improved, and when the polyester is applied to a coating solution for the inner surface of a can, etc., a coating film having excellent hot water resistance may be produced, thereby completing the present invention.

Accordingly, the tricyclodecane dimethanol composition of the present invention satisfies that the total weight of the components A to C with respect to the weight of the component D, i.e., the weight ratio of (A+B+C)/D is 10 to 200, preferably, preferably 12 or more, or 15 or more, and 180 or less, 150 or less, or 140 or less. A polyester produced by using the TCDDM composition satisfying the above range has excellent solubility in solvents due to the high irregularity of the polymer chain, and has a structure, in which moisture is difficult to access to the polymer chain. Therefore, the polyester has excellent hot water resistance even under acidic or basic conditions, and as a result, its hydrolysis does not easily occur.

Further, the tricyclodecane dimethanol composition may further include E) octahydro-4,7-methano-1H-indene-$2_{ax}$, $6_{ax}$-dimethanol(Octahydro-4,7-methano-1H-indene-$2_{ax}$,$6_{ax}$-dimethanol), in addition to the components A to D. The component E is represented by the following Formula 1-5:

[Formula 1-5]

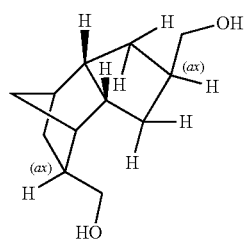

In one embodiment of the present invention, the tricyclodecane dimethanol composition satisfies that the total weight of the components A to C with respect to the weight of the component E, i.e., the weight ratio of (A+B+C)/E is 10 to 200, preferably 12 or more, or 15 or more, and 180 or less, 170 or less, or 160 or less. The TCDDM composition satisfying the above range of the weight ratio may be suitably used in preparing a polyester having high solubility in solvents and exhibiting excellent physical properties without being hydrolyzed when forming a coating film.

In the TCDDM composition, the sum of the components D and E may be 0.5% by weight to 20% by weight, based on the total weight of the composition. When a polyester is produced using a TCDDM composition, in which the total content of the components D and E is less than 0.5% by weight, it is difficult to obtain the effects of improving solubility and inhibiting water penetration due to insufficient irregularity of chains. On the contrary, when a TCDDM composition, in which the total content of the components D and E is more than 20% by weight, is used, a glass transition temperature (Tg) property of the polyester may be deteriorated. For this reason, it is preferable to satisfy the above range. In this point of view, the sum of the components D and E in the TCDDM composition may be more preferably 0.5% by weight or more, or 2.0% by weight or more, and 20% by weight or less, 10% by weight or less, based on the total weight of the composition.

The content of each component in the TCDDM composition may be identified through gas chromatography (GC) analysis.

Specifically, the gas chromatography analysis may be performed under the following conditions. 1 μl of the TCDDM composition is loaded onto a column having a length of 30 m, an inner diameter of 250 m, and a film thickness of 0.25 m. An oven is heated from an initial temperature of 100° C. to 200° C. at a rate of 10° C./min, then heated to 250° C. again at a rate of 3° C./min, held at 250° C. for 30 minutes, and then gas chromatography analysis is performed using nitrogen as a carrier gas under conditions of an inlet temperature of 300° C., a detector temperature of 260° C., a flow rate of 1 mL/min, and a split ratio of 30:1. The analysis conditions may be further specified in exemplary embodiments to be described later.

Under these conditions, the component A is eluted at a retention time of 25.4 min to 25.5 min, the component B is eluted at a retention time of 25.7 min to 25.8 min, the component C is eluted at a retention time of 26.5 min to 26.6 min, the component D is eluted at a retention time of 25.85 min to 25.9 min, and the component E is eluted at a retention time of 26.7 min to 26.8 min. In this regard, the relative content of each compound may be derived by comparing the area of each peak with respect to the total area of the elution peak (excluding the solvent peak) of the TCDDM composition.

Method of Preparing Tricyclodecane Dimethanol Composition

The tricyclodecane dimethanol composition may be prepared by a preparation method including the step of performing a hydrogenation reaction of tricyclodecane dialdehyde in the presence of a hydrogenation catalyst including a support and a catalyst metal supported on the support. In this regard, the support includes one or more elements selected from the group consisting of K, Na, Cr, Fe, Al, Mn, Ba, Si, Zn, Ca, and Bi, and the catalyst metal is one or more selected from the group consisting of Ru, Pd, Pt, Rh, Ni, Cu, and V.

As described above, in the process of preparing TCDDA from DCPD, various structural isomers and stereoisomers of TCDDA are generated. In addition, TCDDA causes tautomerization under acidic or basic conditions, and is converted into different stereoisomers. After TCDDA is hydrogenated and converted to TCDDM, tautomerization may not occur. However, unreacted TCDDA may cause tautomerization in the presence of an acidic or basic hydrogenation catalyst, and as a result, the content ratio of isomers in the prepared TCDDM composition may change.

Accordingly, the present inventors have studied hydrogenation reaction conditions under which the TCDDM composition satisfying the above component ratio may be prepared, and as a result, they found that when the hydrogenation catalyst including the above-described support and catalyst metal is used, it is possible to prepare the TCDDM composition satisfying the weight ratio of (A+B+C)/D in the range of 10 to 200.

The support of the hydrogenation catalyst may be K, Na, Cr, Fe, Al, Mn, Ba, Si, Zn, Ca, or Bi element; oxide of the element; or a salt including the element. For example, the support may be Cr, $Al_2O_3$, $SiO_2$, $TiO_2$, MgO, $Fe_2O_3$, ZnO, $V_2O_5$, BaO, $BaCO_3$, $BaSO_4$, $CaCO_3$, or $MnO_2$.

In one preferred embodiment, the hydrogenation catalyst may be $Ru/Al_2O_3$, $Pt/Al_2O_3$, $Pd/Al_2O_3$, $Pd/BaSO_3$, $Pd/CaCO_3$, $Pd/BaCO_3$, or Cu/Cr.

Meanwhile, the catalyst metal may be supported in an amount of 0.01% by weight to 10% by weight, based on the total weight of the hydrogenation catalyst. When this amount of supporting is satisfied, the isomerization effect of TCDDA may be obtained while maintaining the activity as the hydrogenation catalyst. Preferably, the catalyst metal may be supported in an amount of 0.1% by weight or more, 0.3% by weight or more, or 0.5% by weight or more, and 7% by weight or less, 5% by weight or less, based on the total weight of the hydrogenation catalyst.

During the hydrogenation reaction, the hydrogenation catalyst may be used in an amount of 50 ppm to 10,000 ppm (based on the catalyst metal) of the total weight of TCDDA. When the amount of the catalyst satisfies the above range, the hydrogenation reaction may proceed smoothly without side reactions. Preferably, the hydrogenation catalyst may be used in an amount of 100 ppm to 5,000 ppm, or 500 ppm to 3,000 ppm (based on the catalyst metal) of the total weight of TCDDA.

The hydrogenation reaction may be performed in a solution. As the reaction solvent, a lower alcohol such as methanol, ethanol, isopropanol, etc., water, or a combination thereof may be used. For example, a mixed solvent of water and isopropanol may be used.

The hydrogenation reaction may be performed at a temperature of 80° C. to 250° C. and a pressure of 20 bar to 200 bar, preferably at a temperature of 90° C. to 130° C. and a pressure of 50 bar to 100 bar. When the reaction temperature is lower than 80° C., or the reaction pressure (the pressure of the hydrogen gas) is less than 20 bar, the reaction rate may not be sufficient. When the reaction temperature is higher than 250° C., or the reaction pressure is higher than 200 bar, deactivation of the catalyst may be accelerated, and process costs may increase.

After the hydrogenation reaction, a purification step may be performed, as needed. For example, the reaction mixture may be filtered and subjected to vacuum fractional distillation to obtain the tricyclodecane dimethanol composition. The fractional distillation may be performed, for example, under conditions of a pressure of 0.1 torr to 10 torr, or 0.1 torr to 1 torr and a temperature of 100° C. to 250° C., or 150° C. to 220° C.

Meanwhile, the tricyclodecane dialdehyde (TCDDA) may be prepared through a hydroformylation reaction of dicyclopentadiene (DCPD). Specifically, the TCDDA may be prepared by a preparation method including the steps of performing the hydroformylation reaction by introducing a catalyst composition including a rhodium-containing catalyst compound and an organophosphorus compound into a reactor and adding dropwise dicyclopentadiene under a mixed gas of hydrogen and carbon monoxide; and performing hydrogenation of tricyclodecane dialdehyde obtained by the hydroformylation reaction in the presence of a hydrogenation catalyst.

The catalyst composition used in the hydroformylation reaction includes a rhodium-containing catalyst compound and an organophosphorus compound as a ligand.

The rhodium-containing catalyst compound applicable in the present invention is not particularly limited, as long as it exhibits the hydroformylation activity in the presence of hydrogen and carbon monoxide by forming a complex with the organophosphorus compound. For example, one or more selected from the group consisting of $Rh(acac)(CO)_2$, $Rh_2O_3$, $Rh_4(CO)_{12}$, $Rh_6(CO)_{16}$, $Rh(NO_3)_3$, $Rh(CO_2(C1\sim C8))$, Rh/Al, and Rh/C may be used. Among them, $Rh(acac)(CO)_2$ may be preferably used.

In the known TCDDA preparation method, the rhodium compound is commonly used in an amount of 70 ppm to 300 ppm in order to increase the conversion rate. However, when it is used at such a high concentration, a separate process is further required to recover the expensive rhodium catalyst, and thus there has been a problem in that the efficiency and economic feasibility of the TCDDA preparation process are reduced. In contrast, in the present invention, since hydroformylation is performed by adding dropwise DCPD in small amounts without adding at once, it is possible to obtain excellent TCDDA conversion rate even with a significantly reduced amount of catalyst. Thus, a separate process of recovering the catalyst is not required, thereby greatly improving the efficiency of the process.

In the present invention, the rhodium-containing catalyst compound is preferably used in the range of 1 ppm to 50 ppm, or 10 ppm to 35 ppm, or 10 ppm to 20 ppm (based on the rhodium element) of the total weight of the reactant dicyclopentadiene. When the content of the rhodium-containing catalyst compound is less than 1 ppm relative to the weight of dicyclopentadiene, the amount of the catalyst is too small and the hydroformylation reaction does not properly occur, and therefore, the conversion rate may decrease. When the rhodium-containing catalyst compound is used in excess of 50 ppm, there may be a problem in that impurities due to side reactions are generated, and a separate process of recovering the catalyst is required. Thus, the above-described effect may not be achieved. For this reason, it is preferable to satisfy the above range.

The rhodium-containing catalyst compound may exhibit catalytic activity by forming a complex with an organophosphorus compound in an organic solvent. In this regard, the applicable organophosphorus compound may be phosphine, phosphite, etc., and preferably, phosphite having a formula of $P(OR^1)(OR^2)(OR^3)$ (wherein $R^1$, $R^2$, and $R^3$ are each independently a substituted or unsubstituted alkyl group or aryl group). Specifically, the organophosphorus compound may be one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite, but is not limited thereto.

The amount of the organophosphorus compound may be adjusted according to the content of rhodium in the catalyst composition. In one embodiment, the organophosphorus compound is used in an amount of 5 moles to 200 moles per 1 mole of rhodium. When the content of the organophosphorus compound satisfies the above range, the content of the ligand per catalyst is sufficient, and thus the hydroformylation reaction may proceed smoothly. Preferably, the organophosphorus compound may be used in an amount of 10 moles or more, 15 moles or more, or 25 moles, and 170 moles or less, 150 moles or less, 100 moles or less per 1 mole of rhodium.

The organic solvent applicable to the catalyst composition is not particularly limited, and commonly known inert organic solvents may be appropriately used. Specifically, the organic solvent may include aromatic hydrocarbon compounds, aliphatic hydrocarbon compounds, and alicyclic hydrocarbon compounds.

As the aromatic hydrocarbon compounds, methylbenzenes such as benzene, toluene, xylene, mesitylene, pseudocumene, etc., ethylbenzenes such as ethylbenzene, diethylbenzene, triethylbenzene, etc., propyl benzenes such as isopropylbenzene, 1,3-diisopropyl benzene, 1,4-diisopropyl benzene, etc., and other various alkyl benzenes may also be suitably used. As the aliphatic hydrocarbon compounds, pentane, hexane, heptane, octane, isooctane, dodecane, and decane may be exemplified, but they are not limited thereto, as long as they are a liquid at standard temperature and pressure. As the alicyclic hydrocarbon compounds, cyclohexane, cyclooctane, cyclododecane, decalin, methyl cyclohexane, etc. may be suitably used.

The concentration of the catalyst composition is not particularly limited, but it may be, for example, in the range of 0.01 mM to 5.0 mM, or 0.05 mM to 0.5 mM, based on the rhodium element. When the concentration of the catalyst composition is less than the above range, there may be a problem in that the catalyst reactivity deteriorates due to the excessively low concentration of the catalyst, and when the concentration exceeds the above range, there may be a problem in that the cost of the process increases due to excessive use of the catalyst. Accordingly, the concentration is properly controlled within the above range.

The hydroformylation reaction of DCPD is performed under a mixed gas atmosphere of hydrogen and carbon monoxide, wherein the pressure of the mixed gas is preferably maintained at 20 bar to 150 bar. When the reaction pressure is less than 20 bar, the hydroformylation reaction may not proceed smoothly, and when it exceeds 150 bar, a side reaction may occur to lower the TCDDA yield. More preferably, the pressure of the mixed gas may be 20 bar or more, 30 bar or more, or 50 bar or more, and 120 bar or less, or 100 bar or less.

In this regard, for smooth progress of the hydroformylation reaction, a volume ratio of hydrogen and carbon monoxide is preferably in the range of 1:10 to 10:1, more preferably, in the range of 1:2 to 2:1.

Under the pressure conditions as described above, the temperature of the hydroformylation reaction step is preferably 50° C. to 100° C., more preferably, 70° C. to 90° C., or 75° C. to 85° C. When the reaction temperature is lower than 50° C., smooth progress of the reaction may be difficult and the yield may decrease. When the reaction temperature is too high by exceeding 100° C., the retro Diels-Alder reaction of DCPD and Cp oligomerization by the Diels-Alder reaction of cyclopentadiene (Cp) generated by the retro Diels-Alder reaction and DCPD may occur.

Meanwhile, in the hydroformylation reaction step of the present invention, the raw material DCPD is added in a dropwise manner to the reactor including the catalyst composition, thereby achieving the excellent conversion rate even with a small amount of the catalyst and minimizing side reactions.

When DCPD is added in a dropwise manner, the concentration of DCPD relative to the concentration of the catalyst composition in the reactor is maintained low, and thus Cp oligomerization that may occur in the presence of a high concentration of DCPD may be suppressed. In addition, since the concentration of DCPD in the reactor may be controlled by controlling the dropwise addition rate, a high conversion rate may be achieved even with relatively small amounts of the catalyst compound and the ligand.

DCPD introduced into the reactor may be prepared in the form of a solution. In this regard, as the organic solvent, an organic solvent applicable to the catalyst composition may be used. The organic solvent used for the catalyst composition and the organic solvent used for the DCPD solution are not necessarily the same as each other, but it is preferable that the same solvent is used, because the reaction may smoothly proceed.

The DCPD concentration in the DCPD solution is not particularly limited, and for example, it may be in the range of 0.1 M or more, or 1.0 M to 7.6 M. When the concentration of the DCPD solution is less than the above range, the concentration of the rhodium-containing catalyst compound and the organophosphorus compound in the reactor decreases, as the dropwise addition proceeds, and thus there may be a problem in that the hydroformylation reaction does not proceed smoothly. Accordingly, the concentration is appropriately controlled within the above range.

The dropwise addition rate of DCPD may be controlled according to the concentration of the dicyclopentadiene solution and the capacity of the catalyst composition, and the number of moles of dicyclopentadiene added per minute with respect to 1 mmol of the catalyst (based on the rhodium element) of the catalyst composition is preferably allowed to be 10 mmol to 10,000 mmol, or 100 mmol to 1,000 mmol, or 100 mmol to 500 mmol.

When the dropwise addition rate is too fast by exceeding the above range, it is difficult to achieve the above-mentioned effect due to by-product generation, and when the dropwise addition rate is too slow, the overall reaction rate may become slow, and the process efficiency may be reduced. Accordingly, it is preferable to satisfy the above range.

The reaction mixture including TCDDA which is obtained after the hydroformylation reaction undergoes a purification process such as vacuum distillation, etc., or only a thin film evaporation process to remove the solvent without a separate purification step, and then injected for the hydrogenation reaction. For example, the reaction mixture may be subjected to the thin film evaporation under a pressure of 0.1 torr to 10 torr, or 0.1 torr to 1 torr and a temperature of 90° C. to 150° C., or 100° C. to 120° C. to remove the solvent, followed by the hydrogenation reaction.

The tricyclodecane dimethanol composition prepared by the above-described preparation method may satisfy the weight ratio of (A+B+C)/D in the range of 10 to 200, thereby being suitably used in preparing a polyester having excellent solubility in organic solvents and exhibiting excellent hot water resistance when forming a coating film.

Hereinafter, the actions and effects of the present invention will be described in more detail with reference to the specific exemplary examples of the present invention. However, these exemplary examples are provided only for illustrating the present invention, and the scope of the present invention is not defined thereby.

Preparation of Tricyclodecanedialdehyde

Preparation Example 1

Step 1

In a 1 L high-pressure reactor, 7.9 mg of $Rh(CO)_2(acac)$ (15 ppm, based on Rh, relative to dicyclopentadiene), and 2 g of tris(2,4-di-tert-butylphenyl)phosphite were dissolved in 100 g of toluene, and then the mixture was heated to 85° C. while maintaining a pressure of a mixed gas ($CO:H_2=1:1$) at 100 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

Step 2

The reaction mixture in the step 1 without additional purification was further reacted for 3 hours while heating the mixture to 130° C. and maintaining the pressure of the $CO/H_2$ mixed gas at 100 bar.

Step 3

The reaction mixture of the step 2 was concentrated under reduced pressure to remove toluene. The toluene-removed mixture was subjected to thin film evaporation under conditions of 0.2 torr and 130° C. to obtain 281.1 g (yield: 92.0%) of TCDDA (TCD-dialdehyde).

Preparation and Analysis of Tricyclodecanedimethanol Composition

Comparative Example 1

Step 1

In a 2 L round-bottom flask, 200 g of TCDDA obtained in Preparation Example 1 was mixed with 1 L of methanol, and the temperature was lowered to 0° C. Then, 80 g of $NaBH_4$ was added dropwise over 30 minutes. After completing addition of $NaBH_4$, the temperature was raised to room temperature, followed by stirring for 3 hours. After the reaction was completed, the reaction mixture was concentrated, 1 L of dichloromethane and 1 L of water were added and vigorously stirred, and then the stirring was stopped to separate an organic layer and an aqueous layer. The separated organic layer was concentrated to obtain a mixture including TCDDM (TCD-dimethanol).

Step 2

The mixture including TCDDM obtained in the step 1 was subjected to vacuum fractional distillation under conditions of 150-220° C./0.1 torr to obtain 179 g of a final TCDDM composition.

Comparative Example 2

Step 1

In a 600 ml high-pressure reactor, 100 g of TCDDA obtained in Preparation Example 1, 50 g of isopropyl alcohol (IPA), 12.5 g of water, and 3.0 g of 5% Ru/C(wetted with ca. 50% Water) were mixed and placed, followed by reaction for 4 hours while heating to 130° C. and maintaining a pressure of $H_2$ gas at 70 bar.

Step 2

The reaction mixture of the step 1 was filtered to remove Ru/C, and subjected to vacuum distillation under conditions of 100° C./10 torr to remove isopropyl alcohol and water. The TCDDM mixture thus obtained was subjected to vacuum fractional distillation under conditions of 150-220° C. and 0.1 torr to obtain 181 g of a final TCDDM composition.

Comparative Example 3

A TCDDM composition was prepared in the same manner as in Comparative Example 2, except that 3.0 g of 5% Ru/C (wetted with ca. 50% Water) was used as the hydrogenation catalyst in the step 1.

Comparative Example 4

A TCDDM composition was prepared in the same manner as in Comparative Example 2, except that the pressure of $H_2$ gas in the step 1 was 100 bar.

Comparative Example 5

A TCDDM composition was prepared in the same manner as in Comparative Example 2, except that the pressure of $H_2$ gas in the step 1 was 50 bar.

Comparative Example 6

A TCDDM composition was prepared in the same manner as in Comparative Example 2, except that the reaction temperature in the step 1 was 110° C.

Comparative Example 7

A TCDDM composition was prepared in the same manner as in Comparative Example 2, except that the reaction temperature in the step 1 was 170° C.

Comparative Example 8

A TCDDM composition was prepared in the same manner as in Comparative Example 2, except that 3.0 g of 5% Pd/C (wetted with ca. 50% Water) was used as the hydrogenation catalyst in the step 1.

Comparative Example 9

A TCDDM composition was prepared in the same manner as in Comparative Example 2, except that 1.0 g of 5% Pt/C was used as the hydrogenation catalyst in the step 1.

Example 1

Step 1

In a 600 ml high-pressure reactor, 100 g of TCDDA obtained in Preparation Example 1, 50 g of isopropyl alcohol (IPA), 12.5 g of water, and 30 g of 0.5% $Ru/Al_2O_3$ were mixed and placed, followed by reaction for 4 hours while heating to 110° C. and maintaining a pressure of $H_2$ gas at 70 bar.

Step 2

The reaction mixture of the step 1 was filtered to remove $Ru/Al_2O_3$, and subjected to vacuum distillation under conditions of 100° C./10 torr to remove isopropyl alcohol and water. The TCDDM mixture thus obtained was subjected to vacuum fractional distillation under conditions of 150-220° C. and 0.1 torr to obtain 183 g of a final TCDDM composition.

Example 2

A TCDDM composition was prepared in the same manner as in Example 1, except that the reaction temperature in the step 1 was 130° C.

Example 3

A TCDDM composition was prepared in the same manner as in Example 1, except that the reaction temperature in the step 1 was 150° C.

Example 4

A TCDDM composition was prepared in the same manner as in Example 1, except that the reaction temperature in the step 1 was 170° C.

Example 5

A TCDDM composition was prepared in the same manner as in Example 1, except that 10 g of $Ru/Al_2O_3$ was used in the step 1.

Example 6

A TCDDM composition was prepared in the same manner as in Example 1, except that 60 g of $Ru/Al_2O_3$ was used in the step 1.

Example 7

A TCDDM composition was prepared in the same manner as in Example 1, except that the pressure of $H_2$ gas in the step 1 was 50 bar.

Example 8

A TCDDM composition was prepared in the same manner as in Example 1, except that 30 g of 0.5% $Pd/Al_2O_3$ was used as the hydrogenation catalyst, instead of 0.5% $Ru/Al_2O_3$, and the reaction temperature was 130° C. in the step 1.

Example 9

A TCDDM composition was prepared in the same manner as in Example 1, except that 30 g of 0.5% $Pd/Al_2O_3$ was used as the hydrogenation catalyst, instead of 0.5% $Ru/Al_2O_3$, and the reaction temperature was 170° C. in the step 1.

Example 10

A TCDDM composition was prepared in the same manner as in Example 1, except that 60 g of 0.5% $Pd/Al_2O_3$ was used as the hydrogenation catalyst, instead of 0.5% $Ru/Al_2O_3$, and the reaction temperature was 130° C. in the step 1.

Example 11

A TCDDM composition was prepared in the same manner as in Example 1, except that 30 g of 0.5% $Pd/Al_2O_3$ was used as the hydrogenation catalyst, instead of 0.5% Ru/Al$_2$O$_3$, the reaction temperature was 130° C., and the pressure of H$_2$ gas was 100 bar in the step 1.

Example 12

A TCDDM composition was prepared in the same manner as in Example 1, except that 30 g of 0.5% Pd/Al$_2$O$_3$ was used as the hydrogenation catalyst, instead of 0.5% Ru/Al$_2$O$_3$, the reaction temperature was 130° C., and the pressure of H$_2$ gas was 50 bar in the step 1.

Example 13

A TCDDM composition was prepared in the same manner as in Example 1, except that 30 g of 0.5% Pt/Al$_2$O$_3$ was used as the hydrogenation catalyst, instead of 0.5% Ru/Al$_2$O$_3$, and the reaction temperature was 130° C. in the step 1.

Example 14

A TCDDM composition was prepared in the same manner as in Example 1, except that 30 g of 0.5% Pt/Al$_2$O$_3$ was used as the hydrogenation catalyst, instead of 0.5% Ru/Al$_2$O$_3$, and the reaction temperature was 170° C. in the step 1.

Example 15

A TCDDM composition was prepared in the same manner as in Example 1, except that 3 g of 10% Cu/Cr was used as the hydrogenation catalyst, instead of 0.5% Ru/Al$_2$O$_3$, and the reaction temperature was 130° C. in the step 1.

Example 16

A TCDDM composition was prepared in the same manner as in Example 1, except that 3 g of 10% Cu/Cr was used as the hydrogenation catalyst, instead of 0.5% Ru/Al$_2$O$_3$, and the reaction temperature was 170° C. in the step 1.

Example 17

A TCDDM composition was prepared in the same manner as in Example 1, except that 1 g of 10% Cu/Cr was used as the hydrogenation catalyst, instead of 0.5% Ru/Al$_2$O$_3$, and the reaction temperature was 130° C. in the step 1.

Example 18

A TCDDM composition was prepared in the same manner as in Example 1, except that 3 g of 10% Cu/Cr was used as the hydrogenation catalyst, instead of 0.5% Ru/Al$_2$O$_3$, the reaction temperature was 130° C., and the pressure of H$_2$ gas was 100 bar in the step 1.

Example 19

A TCDDM composition was prepared in the same manner as in Example 1, except that 3 g of 10% Cu/Cr was used as the hydrogenation catalyst, instead of 0.5% Ru/Al$_2$O$_3$, the reaction temperature was 130° C., and the pressure of H$_2$ gas was 50 bar in the step 1.

Example 20

A TCDDM composition was prepared in the same manner as in Example 1, except that 5 g of 5% Pd/CaCO$_3$ was used as the hydrogenation catalyst, instead of 0.5% Ru/Al$_2$O$_3$, and the reaction temperature was 130° C. in the step 1.

Example 21

A TCDDM composition was prepared in the same manner as in Example 1, except that 5 g of 5% Pd/CaCO$_3$ was used as the hydrogenation catalyst, instead of 0.5% Ru/Al$_2$O$_3$, and the reaction temperature was 170° C. in the step 1.

Example 22

A TCDDM composition was prepared in the same manner as in Example 1, except that 5 g of 5% Pd/BaSO$_4$ was used as the hydrogenation catalyst, instead of 0.5% Ru/Al$_2$O$_3$, and the reaction temperature was 130° C. in the step 1.

Example 23

A TCDDM composition was prepared in the same manner as in Example 1, except that 5 g of 5% Pd/BaSO$_4$ was used as the hydrogenation catalyst, instead of 0.5% Ru/Al$_2$O$_3$, and the reaction temperature was 170° C. in the step 1.

Example 24

A TCDDM composition was prepared in the same manner as in Example 1, except that 5 g of 5% Pd/BaCO$_3$ was used as the hydrogenation catalyst, instead of 0.5% Ru/Al$_2$O$_3$, and the reaction temperature was 130° C. in the step 1.

Example 25

A TCDDM composition was prepared in the same manner as in Example 1, except that 5 g of 5% Pd/BaCO$_3$ was used as the hydrogenation catalyst, instead of 0.5% Ru/Al$_2$O$_3$, and the reaction temperature was 170° C. in the step 1.

Analysis of TCDDM Composition: Gas Chromatography (GC)

The contents of isomers in the TCDDM compositions obtained in Examples and Comparative Examples were analyzed by gas chromatography, respectively.

Agilent 7890B (GC-FID) as an instrument and DB-WAX (length of 30 m×inner diameter of 250 m×film thickness of 0.25 m) model as a column were used, and an oven was heated from an initial temperature of 100° C. to 200° C. at a rate of 10° C./min. The temperature was again raised to 250° C. at a rate of 3° C./min, and maintained at 250° C. for 30 minutes, followed by analysis. An inlet temperature was 300° C., a detector temperature was 260° C., a flow rate was 1 mL/min, a split ratio was 30:1, a sample injection volume was 1 μl, and a carrier gas was nitrogen.

Detailed analysis conditions are as follows. The component A was eluted at a retention time of 25.4 min to 25.5 min, the component B was eluted at a retention time of 25.7 min to 25.8 min, the component C was eluted at a retention time of 26.5 min to 26.6 min, the component D was eluted at a retention time of 25.85 min to 25.9 min, and the component E was eluted at a retention time of 26.7 min to 26.8 min. The content (% by weight) of each compound in 100% by weight of the TCDDM composition was derived from the area of each peak with respect to the total area of the elution peak (excluding the solvent peak) of the TCDDM composition.

<Inlet>

Heater: 300° C., Pressure: 13.599 psi, Total Flow: 33 ml/min, Septum Purge Flow: 2 ml/min Split Ratio: 30:1

<COLUMN>
DB-WAX, 30 m×250 m×0.25 m, Agilent
Mode: constant flow, Nominal initial flow: 1.0 mL/min,
Average velocity: 28.23 cm/sec
<DETECTOR (FID)>
Temperature: 260° C. (On), Hydrogen flow: 35.0 mL/min (On), Air flow: 350.0 mL/min (On), Makeup flow: 25.0 mL/min (On)
Makeup Gas Type: Nitrogen When the mixture was slowly heated from room temperature to 240° C. and water or methanol as a by-product flowed out to a theoretical amount, tetrabutoxytitanium was added as a polycondensation catalyst, the temperature was raised to 260° C., and vacuum reaction was carried out for several hours. As a result, copolymerized polyester resins having an intrinsic viscosity of 0.40 dL/g to 0.65 dL/g and a number average molecular weight of 17,000 g/mol to 19,000 g/mol were obtained as in Table 2 below.

TABLE 1

| | Catalyst | Amount of catalyst (ppm)*** | Reaction temperature (° C.) | Reaction pressure (bar) | (A + B + C)/D** | (A + B + C)/E** |
|---|---|---|---|---|---|---|
| Comparative Example 1 | $NaBH_4$ | | | | 499 | 499 |
| Comparative Example 2 | 5% Ru/C* | 1500 | 130 | 70 | 330 | 330 |
| Comparative Example 3 | 5% Ru/C* | 500 | 130 | 70 | 330 | 270 |
| Comparative Example 4 | 5% Ru/C* | 1500 | 130 | 100 | 331 | 332 |
| Comparative Example 5 | 5% Ru/C* | 1500 | 130 | 50 | 356 | 246 |
| Comparative Example 6 | 5% Ru/C* | 1500 | 110 | 70 | 325 | 354 |
| Comparative Example 7 | 5% Ru/C* | 1500 | 170 | 70 | 321 | 342 |
| Comparative Example 8 | 5% Pd/C* | 1500 | 130 | 70 | 410 | 325 |
| Comparative Example 9 | 5% Pt/C | 500 | 130 | 70 | 325 | 352 |
| Example 1 | 0.5% $Ru/Al_2O_3$ | 1500 | 110 | 70 | 61 | 73 |
| Example 2 | 0.5% $Ru/Al_2O_3$ | 1500 | 130 | 70 | 37 | 53 |
| Example 3 | 0.5% $Ru/Al_2O_3$ | 1500 | 150 | 70 | 32 | 43 |
| Example 4 | 0.5% $Ru/Al_2O_3$ | 1500 | 170 | 70 | 25 | 38 |
| Example 5 | 0.5% $Ru/Al_2O_3$ | 500 | 130 | 70 | 30 | 141 |
| Example 6 | 0.5% $Ru/Al_2O_3$ | 3000 | 130 | 70 | 101 | 109 |
| Example 7 | 0.5% $Ru/Al_2O_3$ | 1500 | 130 | 50 | 18 | 31 |
| Example 8 | 0.5% $Ru/Al_2O_3$ | 1500 | 130 | 70 | 43 | 52 |
| Example 9 | 0.5% $Ru/Al_2O_3$ | 1500 | 170 | 70 | 37 | 43 |
| Example 10 | 0.5% $Ru/Al_2O_3$ | 3000 | 130 | 70 | 121 | 152 |
| Example 11 | 0.5% $Ru/Al_2O_3$ | 1500 | 130 | 100 | 43 | 54 |
| Example 12 | 0.5% $Ru/Al_2O_3$ | 1500 | 130 | 50 | 22 | 28 |
| Example 13 | 0.5% $Ru/Al_2O_3$ | 1500 | 130 | 70 | 43 | 69 |
| Example 14 | 0.5% $Ru/Al_2O_3$ | 1500 | 170 | 70 | 34 | 59 |
| Example 15 | 10% Cu/Cr | 3000 | 130 | 70 | 42 | 59 |
| Example 16 | 10% Cu/Cr | 3000 | 170 | 70 | 16 | 33 |
| Example 17 | 10% Cu/Cr | 1000 | 130 | 70 | 20 | 29 |
| Example 18 | 10% Cu/Cr | 3000 | 130 | 100 | 34 | 46 |
| Example 19 | 10% Cu/Cr | 3000 | 130 | 50 | 13 | 15 |
| Example 20 | 5% $Pd/CaCO_3$ | 2500 | 130 | 70 | 35 | 46 |
| Example 21 | 5% $Pd/CaCO_3$ | 2500 | 170 | 70 | 15 | 19 |
| Example 22 | 5% $Pd/BaSO_4$ | 2500 | 130 | 70 | 138 | 159 |
| Example 23 | 5% $Pd/BaSO_4$ | 2500 | 170 | 70 | 98 | 121 |
| Example 24 | 5% $Pd/BaCO_3$ | 2500 | 130 | 70 | 98 | 113 |
| Example 25 | 5% $Pd/BaCO_3$ | 2500 | 170 | 70 | 64 | 87 |

*wetted with ca. 50% Water
**GC area %
***Content of catalyst metal relative to TCDDA Preparation of Polyester Resin and Evaluation of Physical Properties Polyester resins were prepared using the TCDDM compositions of Comparative Examples and Examples by the following method, respectively.

In a 2000 mL four-neck flask equipped with a thermometer, a condenser, a mantle, a stirrer, and a vacuum pump, 549.0 g of terephthalic acid and 6.3 g of trimellitic anhydride as an acid component, 117.9 g of 2-methyl-1,3-propanediol as an alcohol component, and 521.5 g of TCDDM were placed, and tetrabutoxy titanium was added as an esterification catalyst.

Physical properties of the prepared polyester resins were measured by the following methods, and the results are shown in Table 2.

(1) Intrinsic Viscosity (IV)

0.36±0.0002 g of the sample was dissolved in 30 mL of ortho-chlorophenol at 150° C. for 15 minutes, and then the intrinsic viscosity of the sample was measured using a Ubbelohde viscometer in a thermostatic bath at 35° C.

(2) Glass Transition Temperature (Tg)

Using a differential scanning calorimeter (METTLER TOLEDO, DSC 1), about 6 mg to 10 mg of the polyester resin was filled in an aluminum pan, and the polyester resin was heated from room temperature to 280° C. at a rate of 10°

C./min (first scan), and annealed at 280° C. for 3 min. Thereafter, the polyester resin was rapidly cooled to room temperature, and then heated again from room temperature to 280° C. at a rate of 10° C./min (second scan) to obtain a DSC curve.

When the polymer undergoes glass transition, the specific heat of the amorphous material increases, and the DSC curve shows a characteristic shift in the endothermic direction. Therefore, the temperature at which the maximum slope of the curve appeared at the point where the DSC curve showed a first step transition during heating was defined as the glass transition temperature (Tg) of the polyester resin.

(3) Number Average Molecular Weight (Mn) and Weight Average Molecular Weight (Mw)

The number average molecular weight and weight average molecular weight of each resin were measured using Tosoh's gel permeation chromatography (GPC) and RI detector.

0.03 g of the resin was dissolved in 3 mL of ortho-chlorophenol at 150° C. for 15 minutes, and then 9 mL of chloroform was added at room temperature to prepare a sample. The sample was injected at a temperature of 40° C. at a flow rate of 0.7 ml/min using 12 ml of ortho-chlorophenol:chloroform=1:3 (v/v) solution as an eluent for measurement. The values of Mw and Mn were derived using a calibration curve formed using polystyrene standards. 9 kinds of polystyrene standards having a molecular weight of 2,000/10,000/30,000/70,000/200,000/700,000/2,000,000/4,000,000/10,000,000 were used.

(4) Resin Solubility 10 g of the polyester resin was added to 100 g of methyl ethyl ketone and dissolved therein under stirring at 60° C. for 1 hour, followed by cooling to 20° C. After 24 hours, when a transparent homogeneous state was maintained, it was evaluated as good (O), when any one of phase separation or cloudiness occurred, it was evaluated as fair (Δ), and when both of phase separation and cloudiness occurred, it was evaluated as insoluble (X).

TABLE 2

|  | Intrinsic viscosity (dl/g) | Glass transition temperature (° C.) | Mn (g/mol) | Mw (g/mol) | Resin solubility |
| --- | --- | --- | --- | --- | --- |
| Comparative Example 1 | 0.49 | 104.1 | 17700 | 48000 | X |
| Comparative Example 2 | 0.51 | 103.5 | 17200 | 48200 | Δ |
| Comparative Example 3 | 0.50 | 104.3 | 17300 | 47900 | Δ |
| Comparative Example 4 | 0.51 | 103.2 | 18000 | 47300 | Δ |
| Comparative Example 5 | 0.51 | 105.0 | 17400 | 48000 | Δ |
| Comparative Example 6 | 0.49 | 104.3 | 17300 | 47500 | Δ |
| Comparative Example 7 | 0.50 | 103.2 | 17800 | 47300 | Δ |
| Comparative Example 8 | 0.50 | 104.1 | 17500 | 47700 | X |
| Comparative Example 9 | 0.51 | 104.5 | 18000 | 47600 | Δ |
| Example 1 | 0.49 | 105.4 | 17600 | 47900 | O |
| Example 2 | 0.52 | 105.1 | 17300 | 47900 | O |
| Example 3 | 0.5 | 104.4 | 18000 | 48300 | O |
| Example 4 | 0.49 | 104.2 | 18100 | 48100 | O |
| Example 5 | 0.48 | 102.9 | 18100 | 48000 | O |
| Example 6 | 0.50 | 103.4 | 17700 | 47400 | O |
| Example 7 | 0.51 | 104.5 | 17800 | 47600 | O |
| Example 8 | 0.49 | 103.9 | 17500 | 48000 | O |
| Example 9 | 0.49 | 104 | 18200 | 47700 | O |
| Example 10 | 0.50 | 105.1 | 17900 | 47300 | O |
| Example 11 | 0.51 | 104.5 | 17700 | 48000 | O |
| Example 12 | 0.49 | 104.2 | 17700 | 47500 | O |
| Example 13 | 0.52 | 104.0 | 17800 | 47900 | O |
| Example 14 | 0.50 | 103.7 | 17800 | 48100 | O |
| Example 15 | 0.49 | 105.1 | 18000 | 48200 | O |
| Example 16 | 0.48 | 103.3 | 17800 | 47100 | O |
| Example 17 | 0.49 | 103.9 | 17600 | 47300 | O |
| Example 18 | 0.49 | 104.3 | 17800 | 48100 | O |
| Example 19 | 0.51 | 104.4 | 18000 | 47600 | O |
| Example 20 | 0.50 | 103.3 | 17900 | 47300 | O |
| Example 21 | 0.48 | 103.8 | 18100 | 47600 | O |
| Example 22 | 0.52 | 103.4 | 18300 | 47900 | O |
| Example 23 | 0.51 | 103.5 | 17900 | 47300 | O |
| Example 24 | 0.49 | 105.0 | 17800 | 47600 | O |
| Example 25 | 0.50 | 104.1 | 17700 | 48000 | O |

Referring to Table 2, the polyester resins prepared using the TCDDM compositions of Examples 1 to 11 were found to exhibit excellent solubility, as compared to those of Comparative Examples 1 and 2.

<Production of Coating Film and Evaluation of Physical Properties>

Polyester resins having the physical properties of Table 2, each prepared using each of the TCDDM compositions of Examples and Comparative Examples, was diluted with a mixed solvent of Solvent naphtha-100/dibasic ester (5/5, v/v) to obtain a resin solution with a solid content of 40% by weight, and additional components as shown in Table 3 below were blended therewith to prepare a final coating composition with a solid content of 35% by weight.

TABLE 3

| Components in coating composition | Content (g) |
| --- | --- |
| 40% by weight of resin solution (solvent: Solvent naphtha-100/dibasic ester = 5/5, v/v) | 70 |
| 72% by weight of benzoguanamine resin solution (CYMEL 659, Allnex) | 9.7 |
| Solvent naphtha-100 | 10.2 |
| Dibasic ester | 10.1 |
| Dodecylbenzenesulfonic acid (CYCAT 600, Allnex) | 2.0 |

A tin-plated steel plate with a thickness of 0.3 mm was coated with the coating composition at a thickness of 6 m to 10 m, and dried and cured at 210° C. for 10 minutes using an automatic ejecting oven to obtain a plated steel plate on which the coating film was formed.

(1) Evaluation of Hot Water Resistance of Coating Film Under Acidic Conditions

After immersing the plated steel plate in a 3% aqueous acetic acid solution at 100° C. for 3 hours, the degree of cloudiness (damage) on the surface thereof was observed. When no cloudiness was observed, it was scored 10 points out of 10.

In addition, after immersing, a soft cloth was soaked with methyl ethyl ketone (MEK), and wound around the fingers, the surface of the plated steel plate was reciprocally rubbed with the cloth, and the number of reciprocations was counted until the coating film was damaged.

(2) Evaluation of Hot Water Resistance of Coating Film Under Basic Conditions

After immersing the plated steel plate in a 2% aqueous calcium chloride solution at 100° C. for 3 hours, the degree of cloudiness (damage) on the surface thereof was observed. When no cloudiness was observed, it was scored 10 points out of 10.

In addition, after immersing, a soft cloth was soaked with methyl ethyl ketone (MEK), and wound around the fingers, the surface of the plated steel plate was reciprocally rubbed with the cloth, and the number of reciprocations was counted until the coating film was damaged.

TABLE 4

|  | Hot water resistance (acid) | | Hot water resistance (base) | |
| --- | --- | --- | --- | --- |
|  | Cloudiness | Reciprocal rubbing with MEK (number) | Cloudiness | Reciprocal rubbing with MEK (number) |
| Comparative Example 1 | 5 | 7 | 6 | 12 |
| Comparative Example 2 | 6 | 9 | 6 | 14 |
| Comparative Example 3 | 5 | 8 | 6 | 14 |
| Comparative Example 4 | 6 | 9 | 6 | 13 |
| Comparative Example 5 | 4 | 8 | 5 | 13 |
| Comparative Example 6 | 5 | 6 | 5 | 14 |
| Comparative Example 7 | 5 | 7 | 4 | 12 |
| Comparative Example 8 | 5 | 9 | 6 | 11 |
| Comparative Example 9 | 6 | 10 | 5 | 14 |
| Example 1 | 7 | 26 | 7 | 28 |
| Example 2 | 9 | 51 | 9 | 67 |
| Example 3 | 8 | 47 | 9 | 65 |
| Example 4 | 8 | 43 | 8 | 57 |
| Example 5 | 8 | 46 | 8 | 61 |
| Example 6 | 8 | 29 | 9 | 39 |
| Example 7 | 9 | 58 | 9 | 71 |
| Example 8 | 9 | 59 | 9 | 76 |
| Example 9 | 9 | 26 | 9 | 40 |
| Example 10 | 9 | 54 | 9 | 69 |
| Example 11 | 9 | 52 | 9 | 70 |
| Example 12 | 8 | 36 | 9 | 56 |
| Example 13 | 8 | 45 | 9 | 58 |
| Example 14 | 9 | 43 | 8 | 67 |
| Example 15 | 9 | 46 | 9 | 57 |
| Example 16 | 9 | 31 | 8 | 59 |
| Example 17 | 9 | 36 | 9 | 51 |
| Example 18 | 8 | 51 | 9 | 65 |
| Example 19 | 9 | 63 | 8 | 63 |
| Example 20 | 9 | 35 | 8 | 68 |
| Example 21 | 8 | 38 | 9 | 63 |
| Example 22 | 8 | 24 | 9 | 31 |
| Example 23 | 9 | 31 | 9 | 39 |
| Example 24 | 8 | 43 | 8 | 51 |
| Example 25 | 9 | 39 | 8 | 59 |

Referring to Table 4, the coating films obtained from the polyester resins, each prepared using the TCDDM compositions of Examples 1 to 25, were found to have excellent hot water resistance under acidic and basic conditions and to exhibit remarkably improved solvent resistance even after the hot water resistance test, as compared to those of Comparative Examples 1 to 9.

The invention claimed is:

1. A tricyclodecane dimethanol composition comprising
A) octahydro-4,7-methano-1H-indene-1eq,6eq-dimethanol;
B) octahydro-4,7-methano-1H-indene-3eq,6eq-dimethanol;
C) octahydro-4,7-methano-1H-indene-2eq,6eq-dimethanol; and
D) octahydro-4,7-methano-1H-indene-2ax,6eq-dimethanol, wherein a weight ratio of (A+B+C)/D is 15 to 140.

2. The tricyclodecane dimethanol composition of claim 1, further comprising E) octahydro-4,7-methano-1H-indene-2ax,6ax-dimethanol, wherein a weight ratio of (A+B+C)/E is 10 to 200.

3. The tricyclodecane dimethanol composition of claim 2, wherein the weight ratio of (A+B+C)/E is 15 to 160.

4. A method of preparing a tricyclodecane dimethanol composition,
the tricyclodecane dimethanol composition comprising
A) octahydro-4,7-methano-1H-indene-1eq,6eq-dimethanol;
B) octahydro-4,7-methano-1H-indene-3eq,6eq-dimethanol;
C) octahydro-4,7-methano-1H-indene-2eq,6eq-dimethanol; and
D) octahydro-4,7-methano-1H-indene-2ax,6eq-dimethanol,
wherein a weight ratio of (A+B+C)/D is 15 to 140,
the method comprising the step of:
performing a hydrogenation reaction of tricyclodecane dialdehyde in the presence of a hydrogenation catalyst including a support and a catalyst metal supported on the support,
wherein the hydrogenation catalyst is $Ru/Al_2O_3$, $Pt/Al_2O_3$, $Pd/Al_2O_3$, $Pd/BaSO_3$, $Pd/CaCO_3$, $Pd/BaCO_3$, or Cu/Cr, and
wherein the hydrogenation catalyst is used in an amount of 500 ppm to 3,000 ppm (based on the catalyst metal) of the total weight of tricyclodecane dialdehyde.

5. The method of claim 4, wherein the catalyst metal is supported in an amount of 0.01% by weight to 10% by weight, based on the total weight of the hydrogenation catalyst.

6. The method of claim 4, wherein the hydrogenation reaction is performed at a temperature of 80° C. to 250° C. and a pressure of 20 bar to 200 bar.

7. The method of claim 4, wherein the tricyclodecane dialdehyde is prepared by a preparation method including the steps of performing a hydroformylation reaction by introducing a catalyst composition including a rhodium-containing catalyst compound and an organophosphorus compound into a reactor and adding dropwise dicyclopentadiene under a mixed gas of hydrogen and carbon monoxide; and performing hydrogenation of tricyclodecane dialdehyde obtained by the hydroformylation reaction in the presence of a hydrogenation catalyst.

* * * * *